United States Patent
Ohtomo et al.

[11] Patent Number: 5,807,250
[45] Date of Patent: Sep. 15, 1998

[54] BONE ASSESSMENT APPARATUS AND METHOD

[75] Inventors: Naoki Ohtomo, Mitaka; Sadayuki Ueha, 1793-635, Kanamori, Machida-shi, Tokyo, 194, both of Japan

[73] Assignees: Aloka Co., Ltd.; Sadayuki Ueha, both of Tokyo, Japan

[21] Appl. No.: 630,535

[22] Filed: Apr. 10, 1996

[30] Foreign Application Priority Data

Apr. 10, 1995 [JP] Japan .................................. 7-84325

[51] Int. Cl.6 .................................................. A61B 8/00
[52] U.S. Cl. ........................... 600/407; 600/442; 600/437
[58] Field of Search .......................... 128/653.1, 660.01, 128/660.06, 897, 660.03; 600/407, 437, 442, 439

[56] References Cited

U.S. PATENT DOCUMENTS

| | | |
|---|---|---|
| 4,594,895 | 6/1986 | Fujii . |
| 4,619,267 | 10/1986 | Lannuzel et al. . |
| 4,926,870 | 5/1990 | Brandenburger . |
| 4,941,474 | 7/1990 | Pratt, Jr. .............................. 128/660.01 |
| 4,976,267 | 12/1990 | Jeffcoat et al. . |
| 5,042,489 | 8/1991 | Wiener et al. . |
| 5,218,963 | 6/1993 | Mazess ............................... 128/661.03 |
| 5,259,384 | 11/1993 | Kaufman et al. . |
| 5,402,781 | 4/1995 | Dimarogonas . |
| 5,433,203 | 7/1995 | Kimura et al. . |
| 5,651,363 | 7/1997 | Kaufman et al. . |

FOREIGN PATENT DOCUMENTS

| | | |
|---|---|---|
| A-219128 | 4/1987 | European Pat. Off. . |
| WO-A-9420024 | 9/1994 | WIPO . |

*Primary Examiner*—Marvin M. Lateef
*Assistant Examiner*—Shawna J. Shaw
*Attorney, Agent, or Firm*—Fish & Richardson P.C.

[57] ABSTRACT

A bone assessment apparatus for obtaining an assessment value E for a bone (12) with good repeatability by simple calculation using the waveform of a signal derived from received ultrasound which has passed through the bone. A transmitting transducer (20) transmits an ultrasound pulse. A receiving transducer (22) receives the ultrasound pulse which has passed through a test sample (10), and then converts the received ultrasound pulse to a signal. An A/D converter (30) digitizes the signal amplified in a receiving amplifier (28). The digitized signal is inputted to a calculator (32) via a transducer controller (26). The calculator (32) calculates the assessment value E for the bone (12) from characteristic values of the waveform of the signal, such as the half-value width of the first positive portion, which are derived from ultrasonic transmission characteristics of the bone (12).

12 Claims, 6 Drawing Sheets

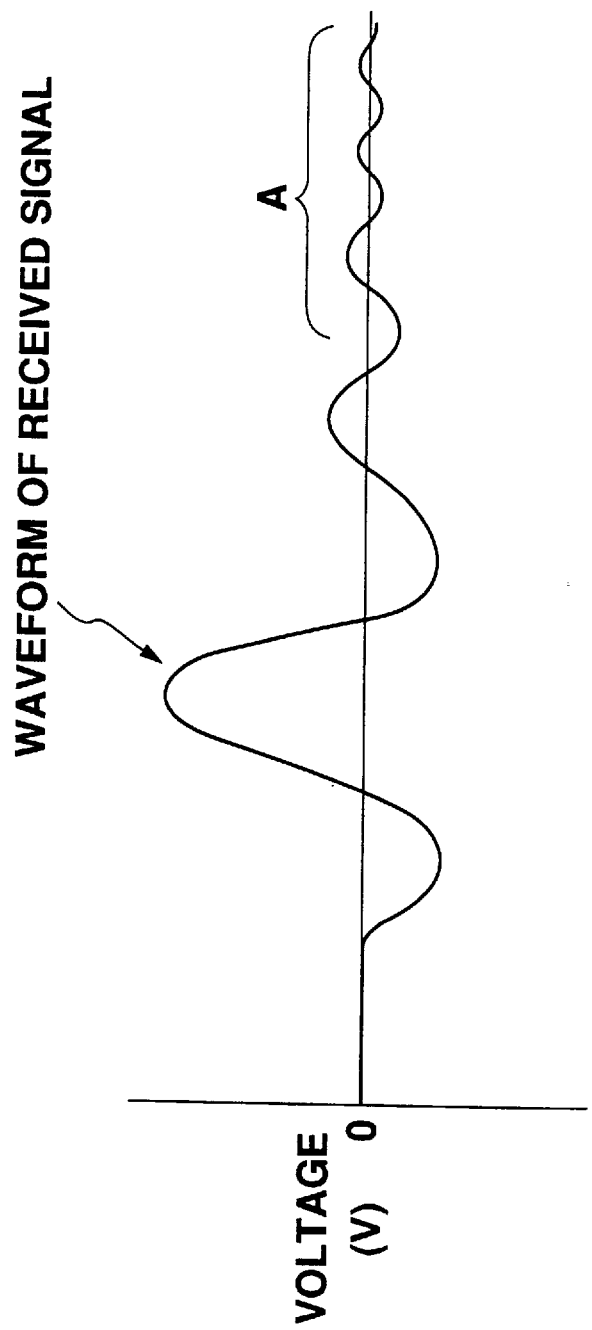

BONE ASSESSMENT APPARATUS AND METHOD

BACKGROUND OF THE INVENTION

1. Field of the Invention

The present invention relates to an apparatus and method for assessing or diagnosing bone tissues using ultrasound.

2. Description of the Prior Art

Due to the rapid increase in the number of elderly people in the population, bone disorders, such as osteoporosis and osteomalacia, have become more common. Therefore, there is an urgent need to develop a better diagnosis or prophylaxis for bone disorders.

Bone mineral density (BMD) measuring apparatuses utilizing X-rays have been conventionally used for the assessment or diagnosis of bone tissues. Recently, a bone assessment apparatus has been proposed, which transmits ultrasound into a living body to assess and diagnose bone tissues. The applicant of the present invention has proposed bone assessment apparatuses utilizing ultrasound in U.S. Pat. No. 5,433,203 or Japanese Patent Laid-Open Publication No. Hei 6-269447.

In an assessment apparatus provided by U.S. Pat. No. 5,433,203, a heel of a subject is placed between a pair of contact probes, and ultrasound transmitted and received between the probes is passed through a calcaneous. A signal derived from the received ultrasound, which has been transmitted through the calcaneous, is converted by Fourier transformation to obtain a transmission spectrum of the ultrasound passed through the calcaneous. An attenuation spectrum, which represents the attenuation of ultrasound at the respective frequencies, is obtained by the difference between the transmission spectrum and an original spectrum of the ultrasound used in this apparatus. The rate of the change in attenuation factor in the attenuation spectrum (gradient of attenuation spectrum) is obtained. The density of a trabecula made of cancellous bone is assessed by the gradient of the attenuation spectrum.

Japanese Patent Laid-Open Publication No. Hei 6-269447 discloses a method for estimating characteristic values (velocity, attenuation coefficient, etc) of ultrasound transmitted in bone tissues. The characteristic values are obtained using a power spectrum or transmittance spectrum of ultrasound passed through a bone tissue by the equivalent transmission-line theory.

According to the above described conventional method, the waveform of the received signal derived from the ultrasound passed through the bone tissue is converted to a spectrum by Fourier transformation in order to obtain an assessment value for the bone tissue.

However, the transmission spectrum for the bone tissue fluctuates to some extent during the measurement. Therefore, the assessment value calculated from the transmission spectrum has low repeatability.

The low repeatability for the assessment value arises from the following:

The waveform of the received signal is varied somewhat with a shift of the measurement position around a diagnosis site of a few millimeters, because the inner structure of a living tissue containing bone is complex. For example, the waveform of a voltage of the received signal derived from ultrasound passed through a calcaneous is shown in FIG. 10. In particular, a trailing portion A of the received signal is rather varied with a slight shift of the measurement position. Therefore, the spectrum of ultrasound transmitted through the calcaneous can be considerably varied among the measurements carried out even for one diagnosis site. This causes the assessment value obtained from the transmission spectrum to have low repeatability.

In addition, complicated calculations, such as Fourier transformation, are needed for obtaining the assessment value by the conventional method, requiring considerable calculation time.

SUMMARY OF THE INVENTION

In order to solve the above problem, the present invention provides a bone assessment apparatus for obtaining an assessment value for a bone tissue, which is derived from ultrasonic transmission characteristics of the bone tissue, by simple processing or calculation with high repeatability.

A bone assessment apparatus provided by the present invention comprises a transmitter for transmitting an ultrasound pulse into a test sample, a receiver for receiving the ultrasound pulse which has passed through the test sample, and a calculator for calculating an assessment value derived from ultrasonic transmission characteristics of the test sample from the waveform of the received ultrasound pulse.

The ultrasound pulse transmitted from the transmitter has frequency components distributed over a wide frequency band. A tissue in the test sample, particularly a bone tissue, operates as a filter range in the ultrasound, and especially cuts off or absorbs high frequency components. Therefore, a signal received by the receiver mainly consists of lower frequency components. In general, the denser the bone tissue, the larger its filter effect becomes. Therefore, the attenuation of high frequency components of a received signal obtained from the measurement of a bone tissue in a patient suffering from a bone disease is smaller than the attenuation of high frequency components in a bone tissue in a healthy person. This causes the shape of the received signal with time to be sharper for the patient than for the healthy person. In the present invention, the characteristic of the waveform of the received signal is utilized. The assessment value of the bone tissue is derived from its ultrasonic transmission characteristics, and directly obtained by the shape of the signal derived from a received ultrasound pulse which has been passed through the test sample. The calculator directly calculates the assessment value of the bone tissue, which is derived from its ultrasonic transmission characteristics, from the shape of the received signal with respect to time.

In a preferred embodiment of the present invention, the width of a predetermined positive or negative portion of the received signal, where the ratio of the width to the height of the portion is a predetermined value, is obtained at a certain level (The peak value of the portion from the horizontal (time) axis is defined as the height). The assessment value is calculated from the width.

In another preferred embodiment, the ratio of the heights of two predetermined portions of the received signal is obtained. The assessment value is calculated from the ratio.

In another preferred embodiment, the area of a first region surrounded by a predetermined portion of the received signal and the time (horizontal) axis, and the area of a second region surrounded by another portion and the time axis are obtained. The assessment value is calculated from the ratio of the areas of the first and second regions.

In another preferred embodiment, the integrals of two predetermined portions of the received signal are obtained. The assessment value is calculated from the ratio of the integrals.

In another preferred embodiment, the received signal is magnified (amplified) or reduced (attenuated) so that a first maximum value of the received signal becomes a predetermined value. The area surrounded by a predetermined portion of the magnified or reduced signal and the time axis is obtained. The assessment value is calculated from the area.

BRIEF DESCRIPTION OF THE DRAWINGS

FIG. 10 shows a typical example of the waveform of a signal derived from ultrasound passed through a calcaneous.

DESCRIPTION OF THE PREFERRED EMBODIMENTS

Figure 1:
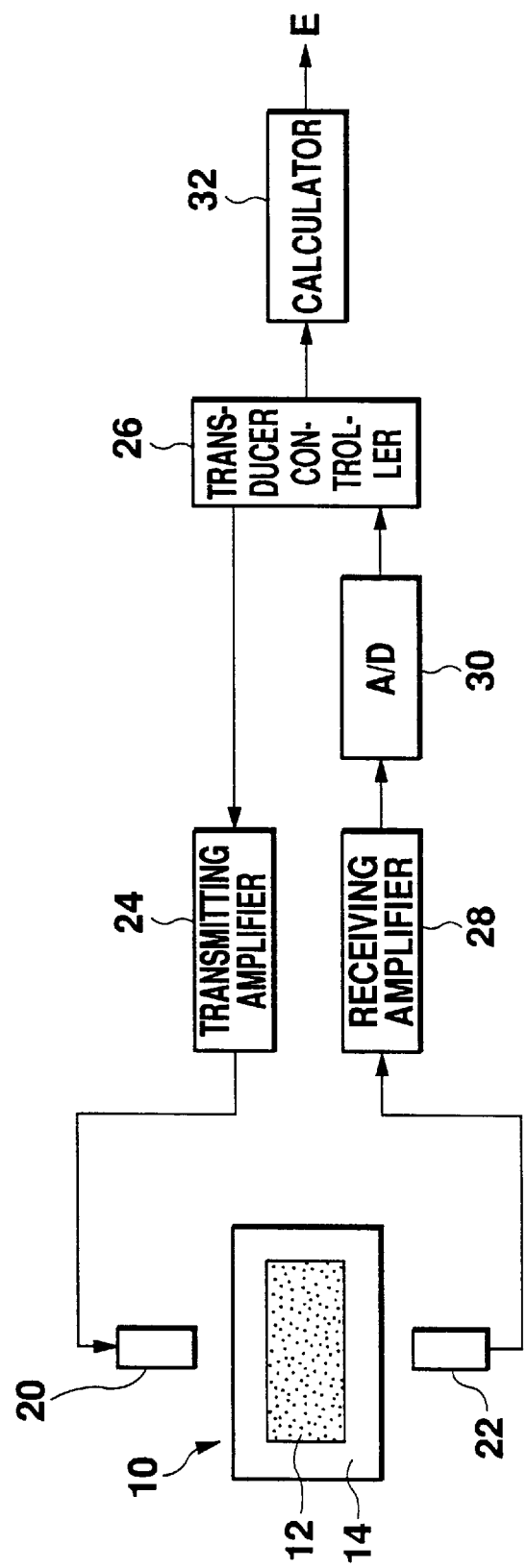
FIG. 1 shows a block diagram of the structure of a bone assessment apparatus provided by the present invention.

Bone assessment apparatuses according to preferred embodiments of the present invention will be described below with reference to drawings. FIG. 1 shows a block diagram of the structure of a bone assessment apparatus according to a preferred embodiment of the present invention.

In FIG. 1, a test sample 10 to be tested comprises a bone 12 and a soft tissue 14. The bone 12 comprises cortical bone located in its outer part and cancellous bone located in its inner part. The degeneration brought about by a bone disease is easily observed in a bone mainly composed of the cancellous bone, such as a calcaneous. Therefore, this bone assessment apparatus uses the calcaneous.

The test sample 10, such as a heel, is placed between a transmitting transducer 20 and a receiving transducer 22. The transmitting transducer 20 is connected to a transmitting amplifier 24. The transmitting amplifier 24 is connected to a transducer controller 26. The transducer controller 26 supplies a transmission trigger signal to the transmitting amplifier 24. The transmitting amplifier 24 supplies a predetermined transmitting pulse in response to the transmission trigger signal to the transmitting transducer 20. The transmitting transducer 20 is driven by the transmitting pulse, and outputs a predetermined ultrasound pulse.

The receiving transducer 22 is connected to a receiving amplifier 28. The receiving amplifier 28 is connected to an A/D converter 30. The A/D converter 30 is connected to the transducer controller 26. The receiving transducer 22 receives an ultrasound pulse passed through the sample 10, and converts it to an electrical signal (received signal). The receiving amplifier 28 amplifies the received signal. The A/D converter 30 digitizes the amplified received signal. The digitized received signal is inputted to a calculator 32 via the transducer controller 26.

The calculator 32 calculates an assessment value E, which is derived from ultrasonic transmission characteristics of the bone 12, from the inputted received signal. The principle of calculating the assessment value E and actual methods for obtaining the assessment value E according to the principle are described below with reference to drawings.

Figure 2:
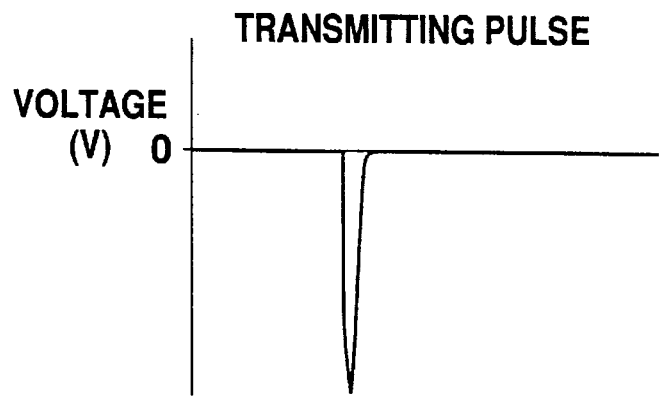
FIG. 2 shows the waveform of a transmitting pulse used in a preferred embodiment of the present invention.

FIG. 2 exemplifies the waveform of voltage of the transmitting pulse supplied to the transmitting transducer 20 shown in FIG. 1. As shown in FIG. 2, the width of the transmitting pulse is very small (in the order of nsec). The transmitting transducer 20 is driven by the very narrow transmitting pulse. The ultrasound pulse transmitted from the transmitting transducer 20 has frequency components distributed over a wide frequency band.

Figure 3A:
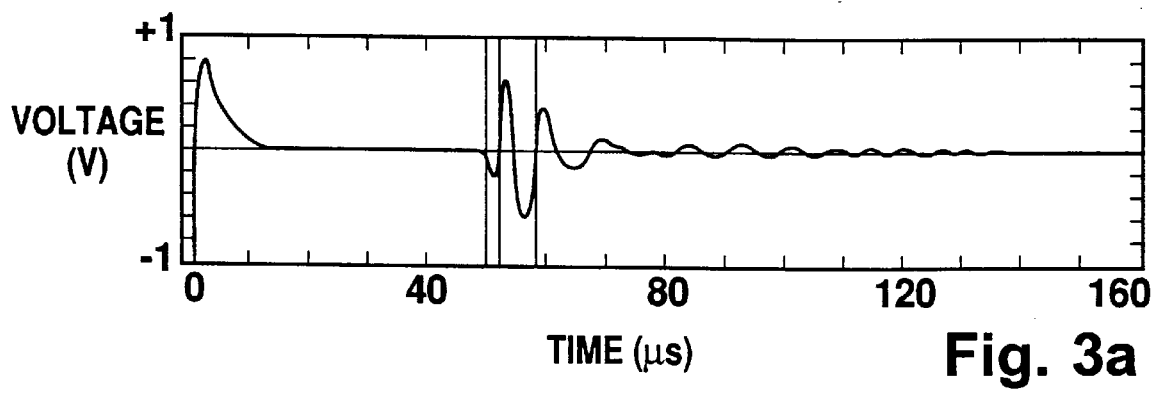
FIG. 3 exemplifies the waveform of a received signal derived from ultrasound passed through a bone tissue of a healthy person.
Figure 3B:
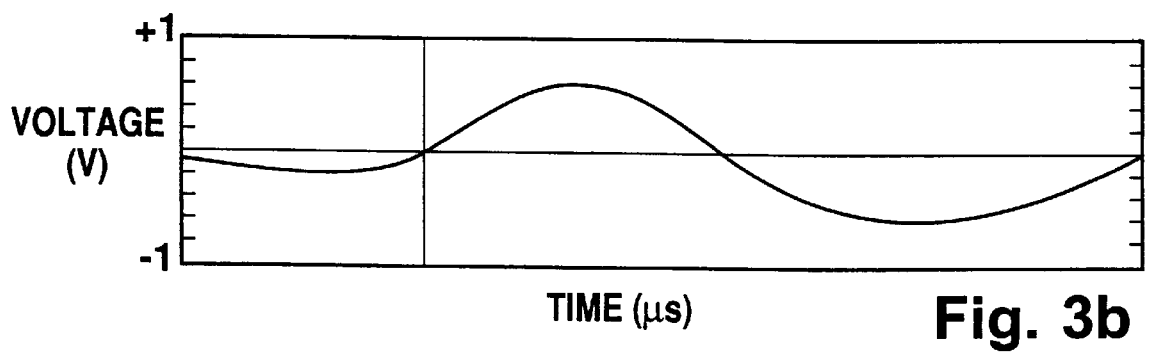
Figure 4A:
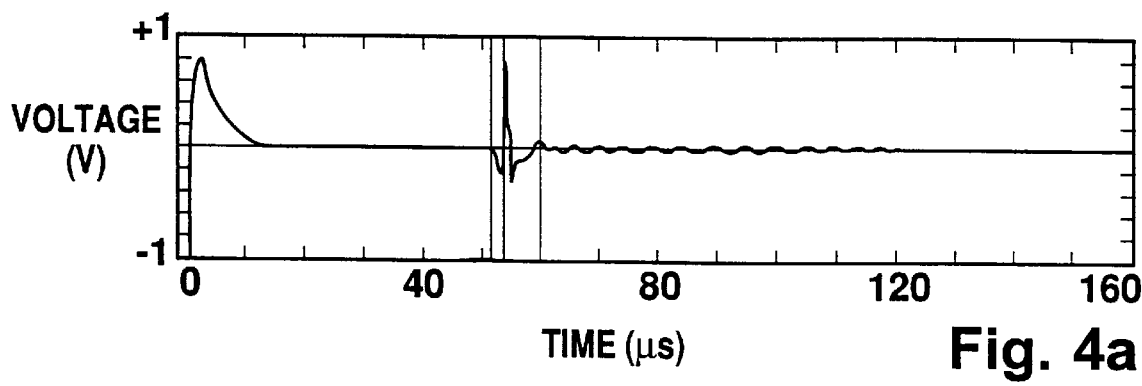
FIG. 4 exemplifies the waveform of a received signal derived from ultrasound passed through bone tissue of a patient suffering from a bone disease.
Figure 4B:
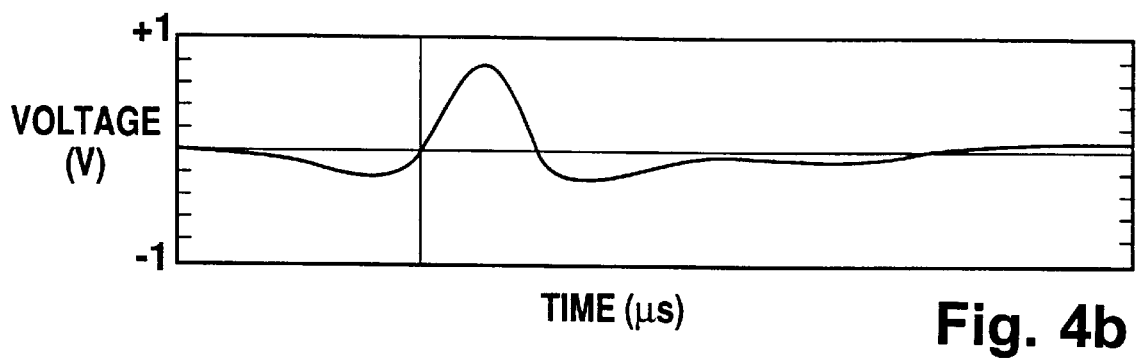

FIGS. 3 and 4 exemplify the waveforms of received signals, which are derived from ultrasound passed through a calcaneous. The horizontal axis and vertical axis in the graphs represent time and signal level (voltage), respectively. Similar patterns of repeating peaks and troughs in the signal are observed in both FIGS. 3 and 4. The pattern of the received signal is generally observed when the transmitting pulse shown in FIG. 2 is received after being passed through a bone.

FIG. 3 shows the waveform of a received signal derived from an ultrasound pulse passed through a calcaneous in a healthy person. As shown in (a) of FIG. 3, the waveform of the received signal is shown over a relatively long time period from the starting point of transmission of the ultrasound pulse. As shown in (b) of FIG. 3, a magnified part of the waveform which represents a characteristic of the ultrasound pulse passed through the calcaneous, is shown for a predetermined time period from the starting point of receiving the ultrasound pulse.

FIG. 4 shows the waveform of a received signal derived from an ultrasound pulse passed through a calcaneous in a patient suffering from a bone disease. As shown in (a) of FIG. 4, the waveform of the received signal is shown over a relatively long period of time from the starting point of transmission of the ultrasound pulse, as in FIG. 3. As shown in (b) of FIG. 4, a magnified part of the waveform which represents a characteristic of the ultrasound pulse passed through the calcaneous is shown for a predetermined time period from the starting point of receiving of the ultrasound pulse. FIG. 4 is drawn to the same time scale as FIG. 3.

As seen in FIGS. 3 and 4, a dense trabecula made of a large amount of bone in a healthy person efficiently cuts off the high frequency components. The high frequency components are well attenuated, causing the waveform of the received signal to be broad. In contrast, a sparser trabecula in a patient suffering from a bone disease, such as osteoporosis, allows the high frequency components to pass through it relatively well, causing the waveform of the received signal to be narrow.

Therefore, the density of a bone can be evaluated by quantifying the narrowness or broadness of the waveform of the received signal.

In this preferred embodiment, the following values are obtained as the assessment value E for quantifying the characteristic of the waveform of the received signal.

Figure 5:
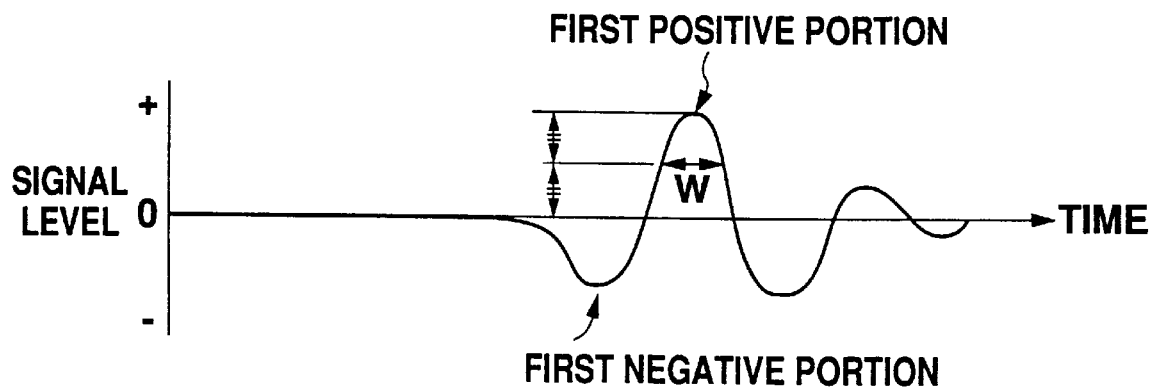
FIG. 5 represents a method for obtaining an assessment value for bone.

(1) Half-value width W of the first positive portion (see FIG. 5).

As described before, the level of the received signal derived from the ultrasound pulse passed through the calcaneous first decreases from the zero volts to a first minimum value, and then increases to a first maximum value above zero volts, repeatedly making positive portions and negative portions. The negative portion represents a part of the received signal below the zero volt line, and the positive portion represents a part of the received signal above the zero volt line.

As described before, a sparser bone in a patient allows the high frequency components of an ultrasound pulse to pass through it quite well. The widths of the peaks in the received signal generally become narrower. The half-value width W of the first positive portion becomes smaller than that for a healthy person. Therefore, the half-value width W of the first positive portion can be used as the assessment value E indicating the condition of the subject bone. When a value representing the characteristic of the first positive portion is used, an assessment value with good repeatability can be obtained.

In this preferred embodiment, the calculator 32 shown in FIG. 1 detects the first positive portion of a received signal inputted from the transducer controller 26, obtains the half-value width W of the first portion, and outputs the half-value width W as the assessment value E.

Figure 6:
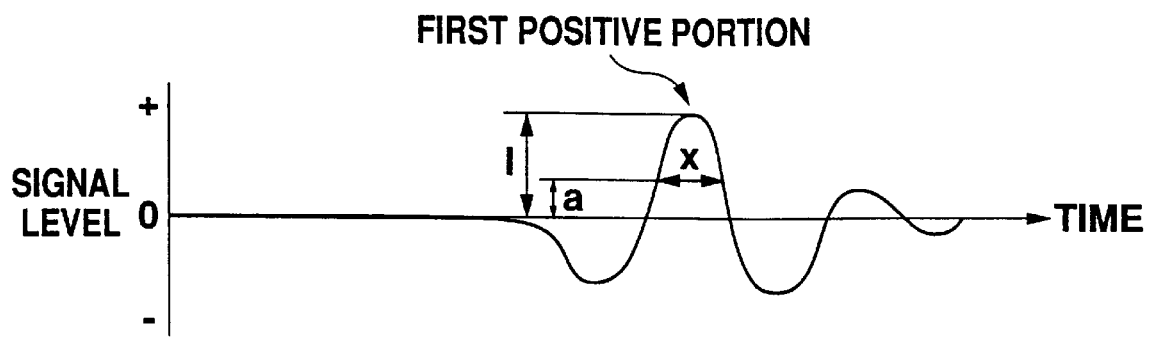
FIG. 6 represents a method for obtaining an assessment value for bone.

A value other than the half-value width W can be used as the assessment value E in this preferred embodiment. As shown in FIG. 6, the width x of the first positive portion, at a level where the ratio of the width to the maximum value (height) of the first positive portion is a predetermined value "a," is used as the assessment value E (maximum value of 1, ratio of "a" in FIG. 6). The ratio "a" suitable for the respective bones can be arbitrarily selected in the range from 0 below 1.

The preferred embodiment here focuses on the first positive portion, because the first positive portion is probably formed by ultrasound passing directly through the subject bone. The height of the first positive portion is generally the largest in the received signal. The first positive portion reflects the condition of the subject bone most accurately, and is probably the most insensitive to changes in measurement conditions. In general, the denser the bone, the more the high frequency components are cut off, leading to a broad shape of the received signal. Therefore, the half-value width (or width at a predetermined level) of any positive or negative portion other than the first positive portion can be used as the assessment value E in principle.

In the above described example, the width of the positive or negative portion of the received signal is the assessment value E. In addition, the ratio of the widths of a positive portion and negative portions can be used as the assessment value E.

Figure 7:
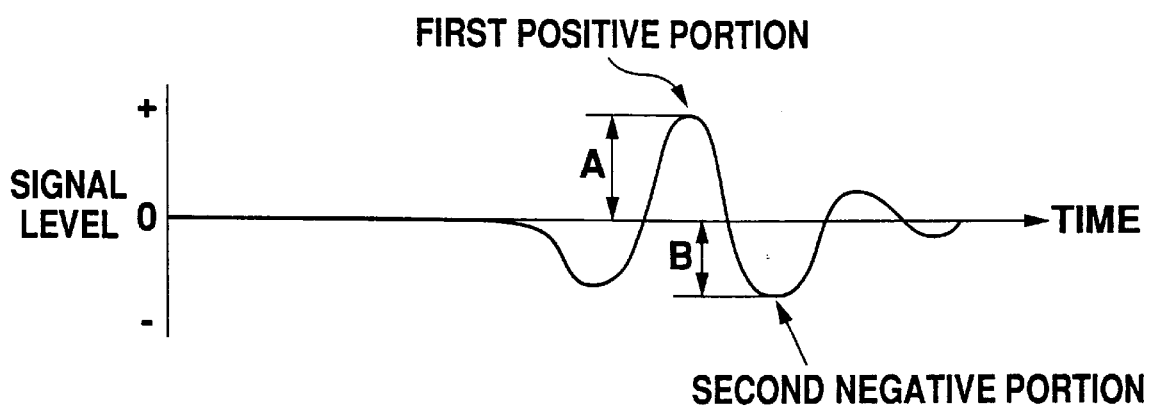
FIG. 7 represents a method for obtaining an assessment value for bone.

(2) Ratio A/B of the height A of the first positive portion and the height B of the second negative portion (see FIG. 7).

The applicant has discovered through experimentation that the ratio A/B for a weakened bone in a patient suffering from a bone disease is larger than that for a dense bone in a healthy person. This phenomenon is assumed to result from the fact that the first positive portion most significantly brings about the attenuation of the high frequency components. When the high frequency components are less attenuated, the shape of the received signal becomes sharper. The sharpening effect appears most markedly in the first positive portion. Consequently, the height (maximum value) of the first positive portion is relatively more enhanced than the heights (maximum values) of the other positive portions or those (minimum values) of negative portions. The applicant has also discovered through experimentation that the ratio A/B is closely related to the bone mineral density (BMD), as well as the gradient of attenuation spectrum described before.

In addition, the applicant has found quite a good correlation between the bone strength and ratio of the heights of positive and negative portions other than the above combination. Therefore, the height ratios derived from any combinations of positive and negative portions other than that of the first positive and the second negative portions can be used as the assessment value E.

When the ratio of the heights of predetermined positive and negative portions is used as the assessment value E, the calculator 32 shown in FIG. 1 detects the predetermined positive and negative portions, and then obtains the ratio of their heights.

Figure 8:
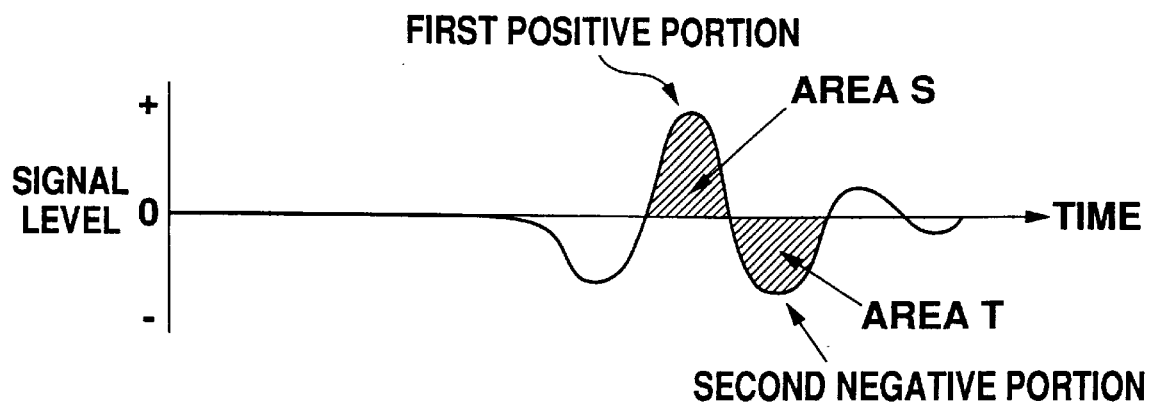
FIG. 8 represents a method for obtaining an assessment value for bone.

(3) Ratio SIT of the area S surrounded by the first positive portion and the time axis and area T surrounded by the second negative portion and the time axis (see FIG. 8).

The ratio SIT for a weakened bone in a patient suffering a bone disease is larger than that for a dense bone in a healthy person. This phenomenon is also assumed to arise for the same reason as that given for the ratio A/B. The ratio SIT can be used as the assessment value E indicating the condition of the subject bone. The ratios of areas derived from any combinations of positive and negative portions other than that of the first positive and the second negative portions can be used as the assessment value E.

When the ratio of the areas of predetermined positive and negative portions is used as the assessment value E, the structure shown in FIG. 1 detects the predetermined positive and negative portions, and then obtains the ratio of their areas. For example, the areas surrounded by the portions and time axis can be obtained by integrating the waveform of the received signal.

Figure 9:
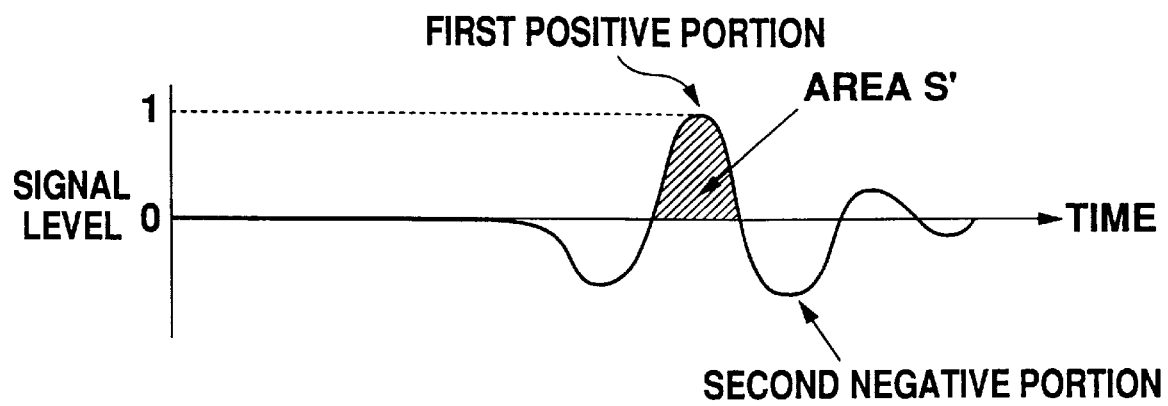
FIG. 9 represents a method for obtaining an assessment value for bone.

(4) Area S' surrounded by the time axis and first positive portion magnified or reduced so that its height (maximum value) becomes unity (see FIG. 9).

In this method, the waveform of the received signal is magnified or reduced so that the height of the first positive portion becomes unity. The area S' surrounded by the time axis and the magnified or reduced first positive portion is calculated. The calculated area S' is used as the assessment value E for the subject bone.

When the subject bone suffers from a bone disease, the shape of the portion in the received signal becomes sharper. Therefore, the normalization of the height of the first positive portion to a predetermined value (for example, unity) makes the area S' for a bone in a healthy person larger than the area S' for a bone in a patient suffering from the bone disease. The area S' can be used as the assessment value E indicating the condition of the subject bone.

The area of any normalized positive or negative portion other than the normalized first positive portion can be used as the assessment value E.

When the area of a predetermined normalized portion in the received signal is used as the assessment value E, the calculator 32 shown in FIG. 1 so magnifies or reduces the waveform of the received signal that the height of the first positive portion becomes a predetermined value, and then obtains the area surrounded by the time axis and a predetermined portion of the magnified or reduced waveform of the received signal.

The assessment values obtained from the waveform of the received signal with time are described above. The applicant has discovered, through experimentation, that the assessment values described above are closely related to the gradient of attenuation spectrum described in U.S. Pat. No. 5,433,203.

The principle of calculating the assessment value and examples of the assessment value are shown above. The assessment value for a bone is not limited to the above shown values themselves. The scope of the present invention covers any assessment value obtained by the combination of any of above described (1), (2), (3) or (4). It also covers any other assessment value obtained by the combination of the assessment value obtained from the waveform of the received signal, and physical properties of the subject bone, such as speed of sound and BMD.

As described above, this preferred embodiment of the present invention focuses on the waveform of the received signal. In a bone assessment apparatus according to this preferred embodiment of the present invention, the assessment value E derived from ultrasonic transmission characteristics of the subject bone can be obtained through fairly simple calculation from a characteristic value defined by the waveform itself. The process for obtaining the assessment value E does not have any complicated calculation, such as is used in a conventional bone assessment apparatus, such as Fourier transformation. In addition, the first peak in the received signal, which is resilient to changes in measuring conditions, is used to improve the repeatability for the obtained assessment value.

While there have been described what are at present considered to be preferred embodiments of the present invention, it will be understood that various modifications may be made thereto, and it is intended that the appended claims cover all such modifications as fall within the true spirit and scope of the present invention.

What is claimed is:

1. A bone assessment apparatus for assessing a test sample of bone through which ultrasound is passed comprising:
   a transmitter for transmitting an ultrasound pulse through the test sample;
   a receiver for receiving the ultrasound pulse which has passed through the test sample; and
   a calculator for calculating an assessment value of the test sample, which is derived from ultrasonic transmission characteristics of the test sample, from the waveform of a signal output from the receiver according to the received ultrasound pulse, wherein the calculator obtains the width of a predetermined positive or negative portion of the signal at a predetermined level, the ratio of the width to the maximum value of the predetermined positive or negative portion being a predetermined value, and calculates the assessment value from the obtained width.

2. A bone assessment apparatus for assessing a test sample of a bone through which ultrasound is passed comprising:
   a transmitter for transmitting an ultrasound pulse through the test sample;
   a receiver for receiving the ultrasound pulse which has passed through the test sample; and
   a calculator for calculating a bone assessment value of the test sample, which is derived from ultrasonic transmission characteristics of the test sample directly from the waveform of a signal output from the receiver according to the received ultrasound pulse;
   wherein the calculator obtains a half-value width of a first positive portion of the signal, and calculates an assessment value from the obtained half-value width.

3. A bone assessment apparatus for assessing a test sample of a bone through which ultrasound is passed comprising:
   a transmitter for transmitting an ultrasound pulse through the test sample;
   a receiver for receiving the ultrasound pulse which has passed through the test sample; and
   a calculator for calculating a bone assessment value of the test sample, which is derived from ultrasonic transmission characteristics of the test sample, directly from the waveform of a signal output from the receiver according to the received ultrasound pulse;
   wherein the calculator obtains a ratio of a maximum value of a first positive portion and a minimum value of a second negative portion, and calculates the assessment value from the obtained ratio.

4. A bone assessment apparatus for assessing a test sample of a bone through which ultrasound is passed comprising:
   a transmitter for transmitting an ultrasound pulse through the test sample;
   a receiver for receiving the ultrasound pulse which has passed through the test sample; and
   a calculator for calculating an assessment value of the test sample, which is derived from ultrasonic transmission characteristics of the test sample, from the waveform of a signal output from the receiver according to the received ultrasound pulse, wherein the calculator obtains the area of a first region surrounded by a predetermined positive or negative portion of the signal and the time axis and the area of a second region surrounded by another predetermined portion and the time axis, computes the ratio of the area of the first region to the area of the second region, and calculates the assessment value from the computed ratio.

5. A bone assessment apparatus in accordance with claim 4, wherein the first region is surrounded by the first positive portion of the signal and the time axis, and the second region is surrounded by the second negative portion of the signal and the time axis.

6. A bone assessment apparatus for assessing a test sample of a bone through which ultrasound is passed comprising:
   a transmitter for transmitting an ultrasound pulse through the test sample;
   a receiver for receiving the ultrasound pulse which has passed through the test sample; and
   a calculator for calculating a bone assessment value of the test sample, which is derived from ultrasonic transmission characteristics of the test sample, directly from the waveform of a signal output from the receiver according to the received ultrasound pulse;
   wherein the calculator obtains integrals of a predetermined positive or negative portion of the signal and of another predetermined positive or negative portion of the signal, and calculates the assessment value from a ratio of the obtained integrals.

7. A bone assessment apparatus for assessing a test sample of a bone through which ultrasound is passed comprising: a transmitter for transmitting an ultrasound pulse through the test sample;
   a receiver for receiving the ultrasound pulse which has passed through the test sample; and
   a calculator for calculating an assessment value of the test sample, which is derived from ultrasonic transmission characteristics of the test sample, from the waveform of a signal output from the receiver according to the received ultrasound pulse, wherein the calculator magnifies or reduces the signal so that the maximum value of the first positive portion becomes a predetermined value, obtains the area surrounded by a predetermined portion of the magnified or reduced signal and the time axis, and calculates the assessment value from the obtained area.

8. A bone assessment apparatus in accordance with claim 7, wherein the calculator calculates the assessment value from the area surrounded by the first positive portion of the magnified or reduced signal and the time axis.

9. A bone assessment apparatus for assessing a test sample of a bone through which ultrasound is passed comprising:

a transmitter for transmitting an ultrasound pulse through the test sample;

a receiver for receiving the ultrasound pulse which has passed through the test sample; and a calculator for calculating an assessment value of the test sample, which is derived from ultrasonic transmission characteristics of the test sample, from the waveform of a signal output from the receiver according to the received ultrasound pulse, wherein the calculator magnifies or reduces the signal so that the maximum value of the first positive portion becomes a predetermined value, and calculates the assessment value from the integral of a predetermined portion of the magnified or reduced signal.

10. A bone assessment method for assessing a test sample through which ultrasound is passed, comprising:

transmitting an ultrasound pulse into the test sample;

receiving the ultrasound pulse which has passed through the test sample; and calculating an assessment value of the test sample, which is derived from ultrasonic transmission characteristics of the test sample, from the waveform of a signal output from the receiver according to the received ultrasound pulse, wherein the assessment value is obtained by calculation from the width of a predetermined positive or negative portion of the signal at a predetermined level, the ratio of the width to the maximum value of the predetermined positive or negative portion being a predetermined value.

11. A bone assessment method for assessing a test sample through which ultrasound is passed, comprising:

transmitting an ultrasound pulse into the test sample;

receiving the ultrasound pulse which has passed through the test sample; and calculating an assessment value of the test sample, which is derived from ultrasonic transmission characteristics of the test sample, from the waveform of a signal output from the receiver according to the received ultrasound pulse, wherein the assessment value is obtained by calculation from the ratio of the area of a first region surrounded by a predetermined positive or negative portion of the signal and the time axis, to the area of a second region surrounded by another predetermined portion and the time axis.

12. A bone assessment method for assessing a test sample through which ultrasound is passed, comprising:

transmitting an ultrasound pulse into the test sample;

receiving the ultrasound pulse which has passed through the test sample; and calculating an assessment value of the test sample, which is derived from ultrasonic transmission characteristics of the test sample, from the waveform of a signal output from the receiver according to the received ultrasound pulse, wherein the assessment value is obtained by calculation from the area surrounded by the time axis and a predetermined portion of the signal so magnified or reduced that a maximum value of the first positive portion becomes a predetermined value.

* * * * *